United States Patent [19]

Jacob et al.

[11] Patent Number: 6,162,464
[45] Date of Patent: Dec. 19, 2000

[54] NON-AQUEOUS COLONIC PURGATIVE FORMULATIONS

[75] Inventors: Leonard S. Jacob, Penn Valley; Taffy J. Williams, Lansdale; Robert D. Krell, Mountainhome, all of Pa.

[73] Assignee: Inkine Pharmaceutical, Inc., Blue Bell, Pa.

[21] Appl. No.: 08/829,080

[22] Filed: Mar. 31, 1997

(Under 37 CFR 1.47)

[51] Int. Cl.$^7$ ............................... A61K 9/48; A61K 9/20
[52] U.S. Cl. ..................... 424/456; 424/451; 424/464; 424/465
[58] Field of Search ................... 424/456, 464, 424/465, 451

[56] References Cited

U.S. PATENT DOCUMENTS

| | | |
|---|---|---|
| 3,088,870 | 5/1963 | McDermott . |
| 3,676,553 | 7/1972 | Reynolds . |
| 3,821,368 | 6/1974 | Reynolds . |
| 4,104,370 | 8/1978 | Bloch ........................... 424/153 |
| 4,432,966 | 2/1984 | Zeitoun . |
| 4,452,779 | 6/1984 | Cockerill . |
| 4,665,100 | 5/1987 | Ludwig . |
| 4,725,427 | 2/1988 | Ashmend et al. . |
| 4,812,311 | 3/1989 | Uchtoman . |
| 4,842,871 | 6/1989 | Hill . |
| 4,904,474 | 2/1990 | Theeuwes . |
| 4,959,222 | 9/1990 | Nadland ........................ 424/692 |
| 5,108,758 | 4/1992 | Allwood . |
| 5,124,144 | 6/1992 | Giorgetti . |
| 5,616,346 | 4/1997 | Aronchick . |
| 5,858,403 | 1/1999 | Borody et al. ................. 424/456 |

FOREIGN PATENT DOCUMENTS

| | | |
|---|---|---|
| 0 484 106 A1 | 5/1992 | European Pat. Off. . |
| 89/09604 | 10/1989 | WIPO . |

OTHER PUBLICATIONS

Physician's Desk Reference; pp. 608–609, 1995 Ed.
Physician's Desk Reference; pp. 699–700; 922–993; & 1826–1827; 1992.
Corazziari, Small Volume Isosmotic Polyethylene Glycol Electrolyte Balanced Solution (PMF–100) in Treatment of Chronic Nonorganic Constipation, Digestive Diseases and Sciences, 41:1636–1642 (1996).

Izzo, The Osmotic and Intrinsic Mechanisms of the Pharmacological Laxative Action of Oral High Doses of Magnesium Sulphate: Importance of the Release of Digestive Polypeptides and Nitric Oxide, Magnesium Research, 9:133–138 (1996).

Liacouras, Whole–Bowel Irrigation as an Adjunct to the Treatment of Chronic, Relapsing *Clostridium Difficile* Colitis, J. Clin. Gastroenterology, 22:186–189 (1996).

Chapman, Antibacterial Activity of Bowel–Cleansing Agents: Implications of Antibacteroides Activity of Senna, Br. J. Surg., 82:1053 (1995).

Goldberg, A Study of a New Osmotic Purgative for Colonoscopy: Is Golytely® Worth its Salt!, Surgical Endoscopy, 9:329–331 (1995).

Izzo, Nitric Oxide as a Mediator of the Laxative Action of Magnesium Sulphate, Br. J. Pharmacol., 113:228–232 (1994).

Bergin, The Effect of Preliminary Bowel Preparation on a Simple Test of Colonic Transit in Constipated subjects, International Journal of Colorectal Disease, 8:75–77 (1993).

Martindale, The Extra Pharmacopoeia, 30$^{th}$ edition, 858–860 (Reynolds ed., 1993).

Araki, A Study of Polyethylene Glycol Electrolyte Lavage Solution and Sodium Picosulfate Combined Pretreatment Method of Colonoscopy, The Kurume Medical Journal, 39:117–121 (1992).

*Primary Examiner*—Thurman K. Page
*Assistant Examiner*—P. McQueeney
*Attorney, Agent, or Firm*—Finnegan, Henderson, Farabow, Garrett & Dunner, L.L.P.

[57] ABSTRACT

Orally administered colonic purgative formulations and methods of its use for effecting partial or complete purgation of the colon in mammals, the formulations consisting of non-aqueous admixtures of a purgative salt selected from the group consisting of $Mg_3(PO_4)_2$, $MgHPO_4$, $Mg(H_2PO_4)_2$, $MgSO_4$, $MgCl_2$, $Na_2SO_4$, sodium tartrate, potassium tartrate, magnesium tartrate and mixtures, thereof, administered in tablet or capsule form in purgative effective concentrations. Preferred embodiments make use of at least one or more magnesium phosphate salts, more preferably dibasic magnesium phosphate; other preferred embodiments include the addition of binders, dispersants and buffers which do not adversely affect osmolality or effectiveness of the purgative formulations.

25 Claims, No Drawings

NON-AQUEOUS COLONIC PURGATIVE FORMULATIONS

This invention relates to colonic purgative formulations based upon inorganic salts and, more particularly, to non-aqueous purgative formulation compositions which may be administered in capsule or tablet form for preparing the colon for surgical or diagnostic procedures.

BACKGROUND OF THE INVENTION

In certain medical procedures, for example, colonoscopy, radiographic examination and in preparation for patients undergoing bowel surgery, it is often critical that the colon be emptied as completely as possible. For example, in order to obtain satisfactory radiographs it is often essential that the intestines be cleansed sufficiently, particularly with regard to the elimination of gas from the colon. The same condition also applies when the colon is preoperatively prepared for surgery, or for diagnostic procedures such as colonoscopies, in which case it is also necessary to remove fecal waste materials.

Typical prior art colonic purgative procedures involved the emptying of the colon using water enemas wherein large quantities of water are introduced into the colon to induce emptying—the contents of the colon being expelled in the form of a suspension. It has, however, been recognized that the use of enemas may be injurious to the patient. In view of the hazard and disadvantages associated with large volume water enemas, an alternative has been to introduce enemas of a hypertonic aqueous solution typically, of various salts to substitute for the large water enema. The advantage of these salt formulations is that they require significantly less water volume in their administration. The effect of these hypertonic enemas is based on the increase of the osmotic pressure in the colon which, in turn, may have undesirable side effects, particularly, if the hypertonic solution diffuses through the wall of the colon and disturbs the fluid balance of the body. Although this is an improvement over simple water enemas, this potential side effect limits the utility of these compositions.

Additionally, many enema compositions in aqueous solutions include a contact laxative agent causing peristalsis in the colon with sufficient concentration of laxation without the need for excessive amounts of water. Such compositions often include salt mixtures and may also contain chemical agents such as propylene glycol and non-ionic wetting agents such as polyether alcohols. The problems with these formulations, aside from the often problematic methods of enema administration, are incomplete evacuation of the bowels, repeat administrations and the inclusion of certain chemicals which may have an irritating effect on the colonic walls. Furthermore, because it is often necessary to employ repeated washout enemas to clear the colon effectively, the potential for such chemical irritation is greatly increased.

More recently, a number of orally administered liquid pharmaceutical compositions have been developed for use as gastrointestinal washes for diagnostic purposes or for use as cathartic laxatives. Such preparations consist of aqueous solutions of polyethylene glycol and electrolytes suchs as sodium sulfate, sodium bicarbonate, sodium chloride and potassium chloride. These orally administered compositions are particularly useful in the rapid washing of the colon for diagnostic purposes. For example, when a powerful gastrointestinal wash is required, such preparations are generally administered in a quantity of about four liters, the composition being typically formulated according to the following: polyethylene glycol 59 g., sodium sulphate 5.68 g., sodium bicarbonate 1.69 g., sodium chloride 1.46 g., potassium chloride 0.745 g. and water to make up one liter. Laxation and relatively thorough evacuation is often significantly improved over enema formulations, and generally without the problems often encountered with enema administrations.

The advantages of using these preparations over other orally administered preparations are a drastic reduction in wash time (from 3–2 days to 4–5 hours) and the minimization of water and electrolyte losses. The advantages which these types of solutions provide are derived from two essential characteristics of the preparation, namely, its isoosmoticity with the physiological liquids, and the balance of the ion species in solution, so as to compensate the transport mechanisms which regulate gastrointestinal absorption. These characteristics result in substantial isotonicity between the preparation and the intracellular and extracellular fluids at the tissues of the digestive tubes walls.

Commercially available products embodying these formulations typically utilize a polyethylene glycol formula serving as a non-absorbable osmotic agent with a mixture of electrolytes for replenishment, so that patients do not become dehydrated. Patients are required to ingest a significant amount of volume for purgation which may include a one eight ounce glass every ten minutes for a total of one gallon of fluid. Due to the fact that the volume is so high, use of this type of formulation is frequently associated with distention and nausea on a significant scale.

Another serious drawback of these known preparations is their unpleasant, bitter, saline taste which in the more sensitive patients can lead to vomiting—thereby preventing ingestion. However, as the requirement of solution isotonicity is necessary to obtain the aforesaid advantages, the introduction of water soluble adjuvants, for example, to alter taste, must be avoided. Even the most common natural sweeteners such as glucose, fructose, saccharose, and sorbitol could change the osmolarity of these solutions and the inclusion of such adjuvants are generally expressly prohibited. Moreover, even altering the unpleasant taste of these preparations with artificial sweeteners or flavorants in these commercial preparations must be avoided as they could also alter the critical isotonicity.

Furthermore, in the aforesaid preparations of the known art, it is also well recognized that the addition of appreciable quantities of substances which can be fermented by the intestinal flora should be avoided. This is because gas could form which could be extremely dangerous in the case of colonoscopy with electrocautery.

In an attempt to avoid the problems associated with the high volume types of preparations, other investigators have utilized ingestible preparations which consist of aqueous solutions of phosphate salts. The aqueous phosphate salt solution produces a tremendous osmotic effect on the intraluminal contents of the bowel and therefore, evacuation of the bowel occurs with a tremendous increase in the influx of water and electrolytes into the colon. This has been developed for the express purpose of decreasing the volume required in colonic purgations. One such preparation basically is comprised of 480 grams per liter monobasic sodium phosphate and 180 grams per liter dibasic sodium phosphate in stabilized buffered aqueous solution and is sold under the brand name Fleets Phospho-Soda™. Patients are typically required to take two three ounce dosages of this preparation, separated by a three hour interval for a total of six ounces, which is a significant reduction compared to large volumes required by other high volume preparations.

The major short-coming of such concentrated aqueous phosphate solution administration is that the aqueous solution is extremely unpalatable, so much so that the recommended dosage form is administered ice cold so as to minimize the objectionable saline taste. Often, patients complain of severe nausea and vomiting, secondary to the extremely salty taste of the preparation. Frequently, patients cannot even tolerate the ingestion of this preparation at the initial dose and often the second dose becomes even more problematic due to the unpalatable extremely salty taste, even when the taste is partially masked by the use of flavoring agents. Thus, while concentrated purgation solutions represent a slight improvement over other methods of inducing purgation, the short comings of these solutions are readily apparent.

From the foregoing, it can be seen that it is desirable to have an orally administered colonic purgative formulation which may be easily and conveniently administered and which avoids the problems and objectionable tastes of known formulations. It can also be seen that it is desirable to have such a purgative formulation which may be administered without large volumes of water necessary in conventional formulations and which avoids other potentially irritant chemicals or chemicals which could effect osmolality.

It is an object of the present invention to provide easily and conveniently administered dosage formulations of effective colonic purgatives.

It is yet another object of the present invention to provide a colonic purgative formulation which provide purgative activity at lower dosages of salt than prior art sodium phosphate tablets.

It is still another object of the present invention to provide a method of administering a colonic purgative with a minimum amount of patient discomfort.

Yet another object of theinstant invention is to provide a formulation for colonic purgatives which avoids the addition of other components which may be broken down by intestinal flora.

These and other objects and advantages of the invention will be evident after reading the following description.

BRIEF SUMMARY OF THE INVENTION

The present invention relates to colonic purgative formulations in which are contained purgative active amounts of a salt selected from the group consisting of $Mg_3(PO_4)_2$, $MgHPO_4$, $Mg(H_2PO_4)_2$, $MgSO_4$, $MgCl_2$, $Na_2SO_4$, potassium tartrate, sodium tatrate and magnesium tartrate and mixtures, thereof, in a stable, nonaqueous tablet dosage form. In one preferred embodiment, the dosage formulation comprises dibasic magnesium phosphate ($MgHPO_4$). In preferred embodiments, the formulation comprises an effective amount of a purgative salt, preferably, dibasic magnesium phosphate, comprising approximately 0.05 to about 2.0 grams per kilogram body weight which may be conveniently administered to the patient in a tablet or capsule form. Preferably, the patient dosage of the purgative salt falls within the range of about 0.1 to about 1.2 grams per kilogram body weight, magnesium phosphate salts, more preferably about 0.2 to 0.7 grams per kilogram bodyweight. In preferred embodiments according to the present invention, the salt is magnesium hydrogen phosphate (dibasic magnesium phosphate) or a mixture of magnesium hydrogen phosphate and magnesium dihydrogen phosphate (monobasic magnesium phosphate).

In other preferred embodiments, the formulation may be a mixture of dibasic magnesium phosphate and monobasic magnesium phosphate wherein the total amount of the two salts falls within the above ranges. The formulations according to the present invention may further include tablet binders, dispersants and/or buffering agents. Further, in other embodiments, the formulation may include tribasic magnesiium phosphate in addition to either monobasic or dibasic magnesium phosphate, or both, within the above ranges.

DETAILED DESCRIPTION OF THE INVENTION

The term "patient" is used throughout the specification to describe an animal, preferably a human, to whom treatment with the compositions according to the present invention is provided. For treatment of those conditions which are specific for a specific animal such as a human patient, the term patient refers to that specific animal. In most instances in the description of the present invention, the term "patient" will refer to human patients.

The term "salt" or "purgative salt" is used throughout the present application to describe one or more of the anhydrous compounds which find use in purgative products according to the present invention. Salts according to the present invention may be found in their anhydrous form or as in hydrated crystalline form (i.e., complexed or crystallized with one or more molecules of water). Purgative salts for use in the present invention include, for example, $Mg_3(PO_4)_2$, $MgHPO_4$, $Mg(H_2PO_4)_2$, $MgSO_4$, $MgCl_2$, $Na_2SO_4$, sodium tartrate, potassium tartrate, magnesium tartrate, or mixtures, thereof. Preferred salts include the magnesium phosphate salts, with a particularly preferred salt being magnesium monohydrogen phosphate (dibasic magnesium phosphate) or a mixture of magnesium monohydrogen phosphate and magnesium dihydrogen phosphate salts. The magnesium phosphate salts are preferred for use in the present invention because of the dual effect which is produced by both the phosphate anion and the magnesium cation. As a result of this dual action, the magnesium phosphate salts may be utilized in the present invention in amounts which are considered "low dose", i.e. in an amount which is unexpectedly low based upon or compared to other salts, such as sodium phosphate salts which find use in anhydrous purgative formulations.

The term "purgative effective amount" or "purgative effective dosage" is used throughout the specification to describe the amount or concentration of purgative salts used in the present invention which is effective for producing a purgative effect, i.e., the elimination or evacuation from the intestines of its contents. In the case of the magnesium phosphate salts, these salts have unexpectedly been found to be advantageously employed in amounts which are significantly lower than for the sodium phosphate salts. The term "purgative active" is used to describe salts according to the present invention which exhibit biological or pharmacological activity in the form of purgative activity.

The term "anhydrous" is used throughout the specification describe the form in which the purgative salts according to the present invention are administered. Anhydrous formulations are those which essentially have excluded water from the formulations, except, in such instances where the salt is hydrated or otherwise complexed with small amounts of water.

The physiology of intestinal secretion and absorption is generally well known as reflected in the reported literature. While not being limited by way of theory, Applicant's invention is believed to function by creating an increase in intra-luminal fluid of the small bowel to a significant degree and/or creating favorable osmotic conditions in the intestine which allows for a net secretion of sodium and water into the lumen. In addition, in certain embodiments which utilize magnesium phosphate anions, the osmotic effect of the phosphate anions in combination with the motility enhancing effect of the magnesium cations create a synergistic purgative effect which makes the magnesium phosphate salts particularly preferred for use in the present invention. This allows for tremendous fluxes of water to be present within the gastrointestinal lumen which exhibits increased motility, thus producing an unexpectedly effective purgative effect.

In producing formulations according to the present invention, in a preferred embodiment, the present invention consists of a dry admixture of dibasic magesium phosphate or a mixture of monobasic and dibasis magnesium phosphate in an anhydrous state. Formulations according to the present invention may be prepared by placing one or more of the purgative salts according to the present invention, in pharmaceutical form, in a ribbon blender or other similar mung apparatus to effect complete mixing of the components. Additional constituents such as tablet binders, dispersants and/or buffering agents in the range of approximately 0.025% to 25% by weight, more preferably about 1% to 5% by weight, may also be included in the admixture. The formulations may be formulated in tablet or capsule form for oral delivery to a patient.

In preferred embodiments according to the present invention, phosphate salts are used, preferably magnesium phosphate salts and more preferably magnesium monohydrogen phosphate or mixtures of magnesium monohydrogen phosphate and magnesium dihydrogen phosphate. In other preferred embodiments, the amount of magnesium dihydrogen phosphate may be substantially reduced or eliminated in its entirety. In these formulations, dibasic phosphate or tribasic phosphate salts such as magnesium dibasic phosphate and magnesium tribasic phosphate may be used alone or in combination as the principal or exclusive form of phosphate in the formulation, while maintaining a complete purgative effect. Other phosphate salts according to the present invention may also be used, but these salts are less preferred. Upon ingestion, phosphate salts cause a tremendous amount of water to be drawn into the gut. This influx of water causes an increase in intraluminal pressure, which in turn exerts a mechanical stimulus causing an increase in intestinal motility. The purgative effect of the phosphate salts appears to be proportionately related to the increase in the anionic state of the phosphate salt and may be differentiated in their mode of action from other salt formulations which are capable of producing a limited cathartic effect. One such salt, magnesium sulfate, for example, exerts its effect via the magnesium cation which causes hypermotility of the gut. Although not being limited by way of theory, it is believed that the magnesium phosphate salts according to the present invention exert their unexpected enhanced activity by virtue of the combined activity of the phosphate anion and magnesium cation, creating a dual effect.

The admixture of the present invention is formed into an easily administered dosage form, such as tablets or into capsules by methods well known in the art. As used herein, the term admixture refers to a formulation which includes at least one purgative salt, preferably a phosphate or magnesium salt, more preferably at least one magnesium phosphate salt and even more preferably magnesium hydrogen phosphate (alone or in combination with another purgative salt, preferably a magnesium phosphate salt) and at least one other component including other phosphate salts or other additives as disclosed herein. When forming tablets containing the purgative formulation, it will be appreciated that the salts can be compressed into a uniform mixture and can optionally include inert diluents such as a tablet binder. Preferably, the tablet binder is a pharmaceutically acceptable binder and is one which produces no appreciable osmotic effects. Examples of useful binders include non-ionic detergents from the Pluronic™ series, such as Pluronic F-68 (a trademark of BASF-Wyandotte Chemicals, defined as a condensate of ethylene oxide with a condensate of propylene oxide and propylene glycol), related non-ionic surfactants, and mechanical adhesives such as polyvinyl alcohol and sodium carboxymethylcellulose, among numerous others. Microcrystalline cellulose (MCC) may also be used to enhance the compactability of the purgative salts into the tablet or capsule form. One of ordinary skill may readily modify the additives combined with the purgative salts according to the present invention in order to optimize the formulations for oral delivery.

In another preferred embodiment of the instant invention, the tablet or capsules may also include inert dispersal agents which will facilitate dissolution of the tablet or capsule contents in the stomach of the patient. Preferably, the dispersal agent is a pharmaceutically acceptable dispersant and is one which also produces no appreciable osmotic effects. Examples of acceptable dispersants include microcrystalline cellulose (which is also useful as a compacting agent) and anhydrous lactose. A preferred dispersal agent is AC-DI-SOL, a cross-linked starch.

In another preferred embodiment of the present invention, the preferred composition may also include a buffering agent to minimize any acid imbalance which may accompany ingestion of the purgative formulation of Applicants' invention. Suitable buffering agents include magnesium hydroxide, aluminum hydroxide, calcium carbonate and magnesium carbonate.

An important characteristic of the colonic purgative formulations of the instant invention is that they function effectively as purgatives when administered in low volume dosages, as compared to known formulations. In this manner, 2 to 12 tablets, and preferably 4 to 10 tablets per dose, depending on tablet size and weight, with only fluids necessary to assist in swallowing the tablets, will provide complete purgation. The dosage may be administered in a single application but may be preferably administered in two applications separated by approximately 2 to 4 hours. Use of the formulations of this invention in tablet form effectively removes the colonic contents without requiring injection of large quantities of water. Conventional purgative products historically and currently available on the market have had to employ much greater liquid volumes in order to obtain the desired result.

The foregoing description is illustrative of the preferred embodiments shown. It is not intended to limit the present invention to the specific formulations shown and described, but instead it will be appreciated that adaptations and modifications will become apparent from the present disclosure and are intended to be within the scope of the claims.

What we claim is:

1. An orally administerable composition in a solid dosage form capable of inducing purgation of the colon of a patient comprising a colonic purgative effective amount of a non-aqueous admixture of a salt selected from the group consisting of $Mg_3(PO_4)_2$, $MgHPO_4$, $Mg(H_2PO_4)_2$, $MgSO_4$, $MgCl_2$, $Na_2SO_4$, sodium tartrate potassium tartrate, magnesium tartrate and mixtures, thereof, and wherein the purgation of the colon is sufficient to prepare the colon for a surgical or diagnostic procedure, wherein the composition in a solid dosage form can be administered directly to a patient in nonaqueous form.

2. The composition of claim 1, where the composition is in the form of a tablet.

3. The composition in a solid dosage form according to claim 1 wherein said salt is a phosphate salt.

4. The composition in a solid dosage form according to claim 3 wherein said phosphate salt is selected from the group consisting of monobasic magnesium phosphate, dibasic magnesium phosphate and tribasic magnesium phosphate.

5. The composition in a solid dosage form of claim 4 wherein said magnesium phosphate salt is included in an amount ranging from about 0.1 to about 1.2 grams per kilogram body weight of said patient.

6. The composition in a solid dosage form of claim 4 wherein said magnesium phosphate salt is dibasic magnesium phosphate included in an amount ranging from about 0.2 to about 0.7 grams per kilogram body weight of said patient.

7. The composition of claim 4, wherein the composition is in the form of a tablet.

8. The tablet of claim 2 further comprising a buffering agent selected from the group consisting of magnesium hydroxide, aluminum hydroxide, calcium carbonate and magnesium carbonate.

9. The tablet of claim 7 further comprising a buffering agent selected from the group consisting of magnesium hydroxide, aluminum hydroxide, calcium carbonate and magnesium carbonate.

10. The tablet of claim 2 further comprising a dispersal agent selected from the group consisting of anhydrous lactose, microcrystalline cellulose and a cross-linked starch.

11. The tablet of claim 9 further comprising a dispersal agent selected from the group consisting of anhydrous lactose, microcrystalline cellulose and a cross-linked starch.

12. The tablet of claim 2 further comprising a binding agent selected from the group consisting of non-ionic detergents, mechanical adhesives and microcrystalline cellulose.

13. The tablet claim 9 further comprising a binding agent selected from the group consisting of non-ionic detergents, mechanical adhesives and microcrystalline cellulose.

14. A method of inducing purgation of the colon in a patient comprising the steps of:

(a) preparing a non-aqueous admixture of a purgative salt selected from the group consisting of $Mg_3(PO_4)_2$, $MgHPO_4$, $Mg(H_2PO_4)_2$, $MgSO_4$, $MgCl_2$, $Na_2SO_4$, sodium tartrate, potassium tartrate, magnesium tartrate and mixtures, thereof to form a purgative formulation;

(b) forming an orally administrable dosage form of said purgative formulation;

(c) orally administering a purgative effective dosage of said formulation to a patient; and (d) allowing said administered dosage to induce purgation.

15. The method of claim 10 wherein step (a) further includes the step of adding to said purgative formulation at least one member selected from the group consisting of buffering agents, dispersal agents and binders.

16. The method of claim 14 wherein said orally administrable dosage form is selected from the group consisting of capsules and tablets.

17. The method of claim 14 wherein the admixture formed in step (a) includes a purgative salt selected from the group consisting of dibasic magnesium phosphate, monobasic magnesium phosphate and mixtures, thereof.

18. The method of claim 17 wherein said purgative salt is dibasic magnesium phosphate included in an amount ranging from about 0.2 grams per kilogram body weight to 12.0 grams per kilogram body weight.

19. The method of claim 17 wherein said purgative salt is a mixture of dibasic magnesium phosphate and monobasic magnesium phosphate included in an amount ranging from about 0.2 grams per kilogram body weight to 12.0 grams per kilogram body weight.

20. The method of claim 18 wherein said dibasic magnesium phosphate is administered at a rate of from about 0.2 grams per kilogram body weight to 0.7 grams per kilogram body weight.

21. The method of claim 14 wherein step c) is repeated at least once.

22. The method of claim 17 wherein step c) is repeated at least once.

23. The method of claim 16 wherein the capsule is a gelatin capsule.

24. The composition in a solid dosage form of claim 3 wherein said phosphate salt is dibasic magnesium phosphate or a mixture of dibasic magnesium phosphate and monobasic magnesium phosphate.

25. The composition in a solid dosage form of claim 1 wherein said salt is included in an amount ranging from about 0.05 grams per kilogram body weight to about 2.0 grams per kilogram body weight of said patient.

* * * * *